United States Patent
Taron et al.

(10) Patent No.: US 8,288,337 B2
(45) Date of Patent: *Oct. 16, 2012

(54) COMPOSITIONS AND METHODS RELATING TO ELUTABLE CARBOHYDRATE-BINDING PROTEINS

(75) Inventors: Christopher H. Taron, Essex, MA (US); Paul A. Colussi, Gloucester, MA (US); Jeremiah Read, Rockport, MA (US)

(73) Assignee: New England Biolabs, Inc., Ipswich, MA (US)

( * ) Notice: Subject to any disclaimer, the term of this patent is extended or adjusted under 35 U.S.C. 154(b) by 513 days.

This patent is subject to a terminal disclaimer.

(21) Appl. No.: 12/399,075

(22) Filed: Mar. 6, 2009

(65) Prior Publication Data

US 2009/0247423 A1    Oct. 1, 2009

Related U.S. Application Data

(62) Division of application No. 11/524,015, filed on Sep. 20, 2006, now Pat. No. 7,732,565.

(60) Provisional application No. 60/718,657, filed on Sep. 20, 2005.

(51) Int. Cl.
*C07K 14/00* (2006.01)
*C12P 21/00* (2006.01)

(52) U.S. Cl. .............. 514/2; 435/69.7; 435/200
(58) Field of Classification Search .............. None
See application file for complete search history.

(56) References Cited

U.S. PATENT DOCUMENTS

| | | |
|---|---|---|
| 5,643,758 A | 7/1997 | Guan et al. |
| 6,897,285 B2 | 5/2005 | Xu et al. |
| 6,984,505 B2 | 1/2006 | Xu et al. |
| 6,987,007 B2 * | 1/2006 | Xu et al. .............. 435/69.7 |
| 7,060,465 B2 | 6/2006 | Xu et al. |
| 7,390,636 B2 | 6/2008 | Taron |
| 2005/0227326 A1 | 10/2005 | Taron et al. |
| 2006/0035333 A1 | 2/2006 | Taron et al. |
| 2006/0199225 A1 | 9/2006 | Taron |

FOREIGN PATENT DOCUMENTS

WO    WO 2006/041849    4/2006

* cited by examiner

*Primary Examiner* — Anand Desai
(74) *Attorney, Agent, or Firm* — New England Biolabs, Inc; Harriet M. Strimpel

(57) ABSTRACT

Compositions and methods are provided for creating and identifying mutant carbohydrate-binding proteins that reversibly bind to carbohydrate substrates under conditions where the native protein remains bound. Examples of modified chitin-binding domains are provided which can be eluted from chitin in the presence of a reducing agent or at a pH within the range of 5-10.

10 Claims, 3 Drawing Sheets

FIG. 2A

K1CBD$_{WT}$
(SEQ ID NO:1)      DSWAVTRAKELNEQFVKGELNGKDSCSDGEISCTADGKIAICNYGAWVYTECAAGTTCFAYDSGD

K1CBD$_{P1G2}$
(SEQ ID NO:2)      DSWAVTRAKELNEQFVKGELNGKDSCSDGEISCTADGKIAICNYGAWVYTECAASTTCFAYDSGD
                   |                                                       |
                   470                                                     524

FIG. 2B

BcChBD$_{WT}$
(SEQ ID NO:3)      TTNPGVSAWQVNTAYTAGQLVTYNGKTYKCLQPHTSLAGWEPSNVPALWQLQ

BcChBD$_{M6}$
(SEQ ID NO:4)      TTNPGVSAWQVNTAYTAGQLVTYNGKTYKCLQHHTSLAGWEPSNIPALWQLQ
                   |                              |       |
                   648                            680     692

COMPOSITIONS AND METHODS RELATING TO ELUTABLE CARBOHYDRATE-BINDING PROTEINS

CROSS REFERENCE

This application is a divisional application of U.S. application Ser. No. 11/524,015 filed Sep. 20, 2006, which claims priority from U.S. provisional application No. 60/718,657 filed Sep. 20, 2005.

BACKGROUND

Affinity chromatography can be applied to the purification of tagged proteins expressed from any recombinant system including proteins expressed in bacteria, insect and mammalian cells or secreted from yeast. Typically, DNA encoding a peptide sequence such as an antibody epitope or a hexahistidine motif is engineered in-frame with the gene to be expressed and purified. Following expression, the tagged protein is immobilized on a matrix that specifically interacts with the chosen tag allowing the removal of non-specific proteins through a series of washing steps. Elution of the purified protein is often accomplished by the use of competitive peptides or imidazole displacement of the tagged protein from antibody conjugates or nickel resins, respectively.

An advantage that affinity chromatography offers, over traditional chromatography such as anion/cation exchange, size exclusion or hydrophobic chromatography, is that development of purification procedures for individual recombinant proteins is simplified. However, the expense of many affinity matrices, particularly those coupled to antibodies, precludes processing large volumes of cell lysate or spent culture medium cost-effectively.

Carbohydrates represent an abundant and relatively cost-effective chromatography reagent where the effectiveness of a particular material is determined by specific carbohydrate-binding proteins or domains that bind to these reagents. Examples include amylose to which maltose-binding protein binds (U.S. Pat. No. 5,643,758) and chitin to which chitin-binding domain (ChBD) binds (U.S. Pat. Nos. 5,643,758, 6,897,285, 6,984,505, and 7,060,465, and U.S. international application Pub. Nos. WO2006/041849, WO2006/0035333, and WO2005/0227326). The uses of carbohydrates in affinity chromatography depend on the binding affinity between binding proteins and carbohydrates. For some applications, it is desirable that the carbohydrate-binding molecule binds tightly to the carbohydrate where in other applications, it is desirable that the carbohydrate bind reversibly to the carbohydrate-binding molecule so that the carbohydrate-binding molecule may be readily eluted. A method for generating mutant carbohydrate-binding molecules with the desired binding affinity would enable the generation of a range of carbohydrate-binding molecules suitable for different applications.

SUMMARY

In one embodiment of the invention, a method is provided for identifying a mutant carbohydrate-binding protein, for example ChBD or maltose-binding domain, having a desired binding affinity to a carbohydrate, for example chitin or amylose, that includes the steps of: (a) forming a library of cell clones, for example yeast such as *Klyveromyces* or *Bacillus* that express a fusion protein; and (b) identifying the mutant carbohydrate-binding protein with the desired binding affinity, for example by an ELISA assay or a Western Blot.

In an embodiment of the invention, the protein is a fusion protein comprising a randomly mutated carbohydrate-binding protein and a reporter protein.

In an embodiment of the invention, the desired binding affinity of the carbohydrate-binding domain is assessed under predetermined conditions for binding to a carbohydrate substrate, for example a matrix coated with the carbohydrate.

In a further embodiment of the invention, a mutant protein is provided that is capable of reversibly binding a carbohydrate substrate under conditions where the non-mutated carbohydrate-binding protein remains irreversibly bound. The mutated carbohydrate-binding protein binds to the carbohydrate under substantially the same conditions as a non-mutated carbohydrate-binding protein, but the mutated carbohydrate-binding protein is capable of being eluted from carbohydrate in the presence of a reducing agent such as β-mercaptoethanol and DTT or at a pH in the range of pH 5-10, for example pH in the range of 7-9. An example of a carbohydrate-binding protein is ChBD that binds chitin substrate. Examples of ChBDs include *Bacillus* ChBD and yeast (for example *Kluyveromyces*) ChBDs. An example of a mutant *Bacillus* ChBD with the desired properties is where a mutation has been introduced at P680H and V692I. An example of a mutant *Kluyveromyces* ChBD is where a mutation has been introduced at G524S or G524T and includes a C-terminal truncation. An additional example of a mutant *Kluyveromyces* ChBD is one in which a mutation is introduced at G524S or G524T and includes a C-terminal truncation with an additional mutation at the remaining C-terminal end where the additional mutation is at least one of F542L, T543L or I544Y.

Step 1: Form a fusion gene between the reporter and a mutated ChBD.

Step 2: Transform the fusion protein into competent cells grown in standard growth medium.

Step 3: Incubate secreted protein in chitin-coated microtiter well dishes.

Step 4: Compare negative control with experimental elution.

Step 5: ELISA analysis of reporter molecules.

FIG. 2A shows the amino acid sequences for a wild type and mutated ChBD (SEQ ID NOS:1 and 2) from *K. lactis* (KlCTSI) showing mutated residues by means of an "*". The first amino acid in the ChBD is 470 amino acids of the *K. lactis* CTS1 chitinase from which it is derived. The entire chitinase sequence can be found in GenBank M 57601. Even in a fusion protein, the first residue of the ChBD of *K. lactis* is identified as amino acid #470.

FIG. 2B shows the amino acid sequences of the wild type and mutated ChBD (SEQ ID NOS:3 and 4) from *Bacillus circulans* ChiAI showing the mutated residues by an "*". The first amino acid in the ChBD is 648 amino acids of the *B. circulans* ChiA chitinase. The entire sequence of the *B. circulans* ChiA chitinase can be found in GenBank XM_452410. Even in a fusion protein, the first residue of the ChBD of *Bacillus* is identified as 648 amino acids.

Figure 3A:
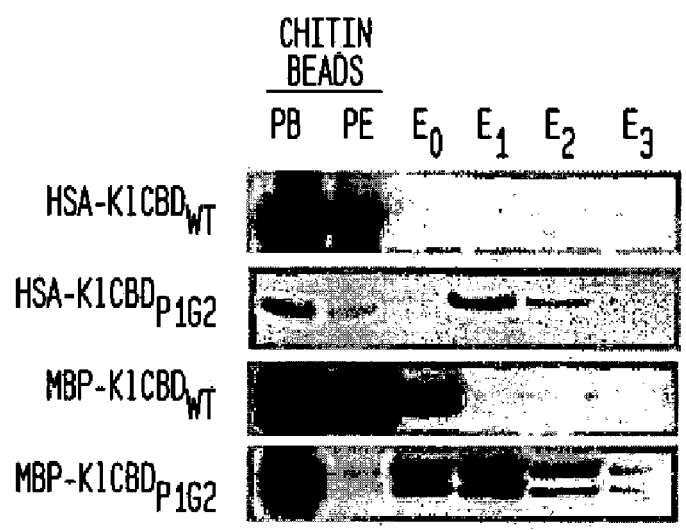

FIG. 3A shows chitin beads with maltose-binding protein (MBP) and HSA *K. lactis* ChBD fusion proteins, both mutated and non-mutated. PB=post binding; PE=post elution, EO, E1, E2, E3 (where E is an elution fraction).

Figure 3B:
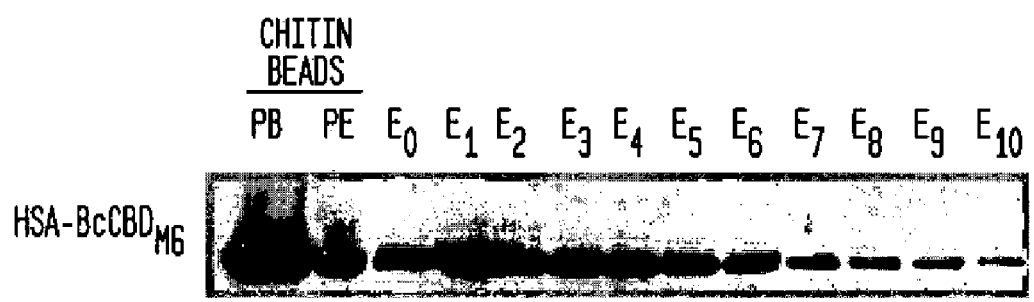

FIG. 3B shows HSA-BcChBD$_{m6}$ eluted from chitin beads at pH 8.

DETAILED DESCRIPTION OF THE EMBODIMENTS

Carbohydrate- (e.g. mono-, di- or polysaccharide) binding proteins for use in embodiments of the present invention include for example: chitin-binding protein, maltose-binding protein, arabthose-binding protein, cellulose-binding protein, arabinogalactan-binding protein and lectin-binding proteins. Although the screening method for identifying mutants of carbohydrate-binding proteins with improved properties is here exemplified by ChBD, the method is applicable to any carbohydrate-binding domain. ChBD is a component sequence of chitinase, which is encoded by DNA from organisms as diverse as viruses, yeast and humans. As its name suggests, ChBD specifically interacts with chitin, which is a β-1,4-linked unbranched polymer of N-acetylglucosamine (GlcNAc) and the second most abundant polymer on earth following cellulose.

In one embodiment, DNA encoding ChBD is fused to a DNA encoding target protein and the fusion protein is expressed in a suitable host cell and preferably secreted into the culture medium. A suitable host cell is one that preferably expresses little or no native ChBD and is capable of being transformed (or transfected) to express and preferably secrete adequate amounts of the fusion protein. Examples of suitable host cells include yeast such as *Kluyveromyces*, for example *Kluyveromyces lactis* or bacteria such as *Bacillus*, for example, *Bacillus circulans*. Where *K. lactis* is used as a production organism for forming a fusion protein, a chitinase-negative or chitinase-down-regulated strain of *K. lactis* may be used to avoid competitive binding to chitin of native chitinase with ChBD fusion proteins (U.S. patent application Pub. No. 2006/0035333).

The fusion protein whether secreted or released from lysed cells can be purified from culture media or lysate by binding to a matrix containing the carbohydrate, for example chitin, to which the binding protein, for example ChBD binds. Examples of matrices include beads, columns and coated surfaces. For example, for ChBD, the matrix may include chitin beads more particularly magnetic chitin beads, colloidal chitin or environmental chitin. The chitin may also be immobilized in a column or coated on a solid surface. In one example, sterile chitin beads are added directly to culture medium so that protein production and harvesting can occur simultaneously during the fermentation process (see for example U.S. patent application Pub. No. 2006/041849).

Once the matrix has been washed to remove contaminating molecules, it is often desirable to elute the fusion protein from the matrix under non-denaturing conditions. However, unmodified ChBD fusion protein cannot be readily eluted from chitin.

To overcome the problem of non-elution of unmodified ChBD, rational mutagenesis was used to generate mutants of ChBD (U.S. Pat. Nos. 6,897,285, 6,984,505 and 7,060,465). Mutants were obtained in which ChBD bound to chitin if a salt was added to the cell lysate prior to binding. The protein could then be eluted from the chitin under non-denaturing conditions. While a mutant of this type is suitable for purification of a ChBD fusion protein from concentrated cell lysates such as occurs with a bacterial expression system, it is less suited for the purification of diluted secreted protein in large culture volumes. In these conditions, a mutant ChBD would be preferred for which the eluant buffer could be modified rather then the spent medium to effect the elution of the ChBD from chitin.

A mutant ChBD with the desired modified functionality was identified using a screening method that relied on random mutagenesis to generate a library of mutants. This approach is summarized in FIG. 1, which in one embodiment describes a screening method and involves the following steps:

(a) creating clonal libraries where a reporter protein is fused in-frame to randomly mutated carbohydrate-binding protein generated by for example error prone PCR;

(b) plating cells secreting mutant fusion proteins in a high-throughput format and then determining their ability to bind and become eluted from chitin deposited in the wells of microtiter plates using a predetermined set of conditions and elution buffer components; and (c) determining the amount of carbohydrate-binding protein remaining in the microtiter plates using ELISA or Western Blot analysis.

Alteration of elution conditions in the above screen resulted in the discovery and isolation of mutants capable of dissociating from carbohydrate under the desired conditions.

The screening method described above was used to identify ChBDs for which elution conditions included one or more of the following: eluant with a pH in the range of pH 5-10, more specifically in the range of pH 7-9, addition of reducing conditions or a selected non-denaturing salt concentration.

Figure 1:
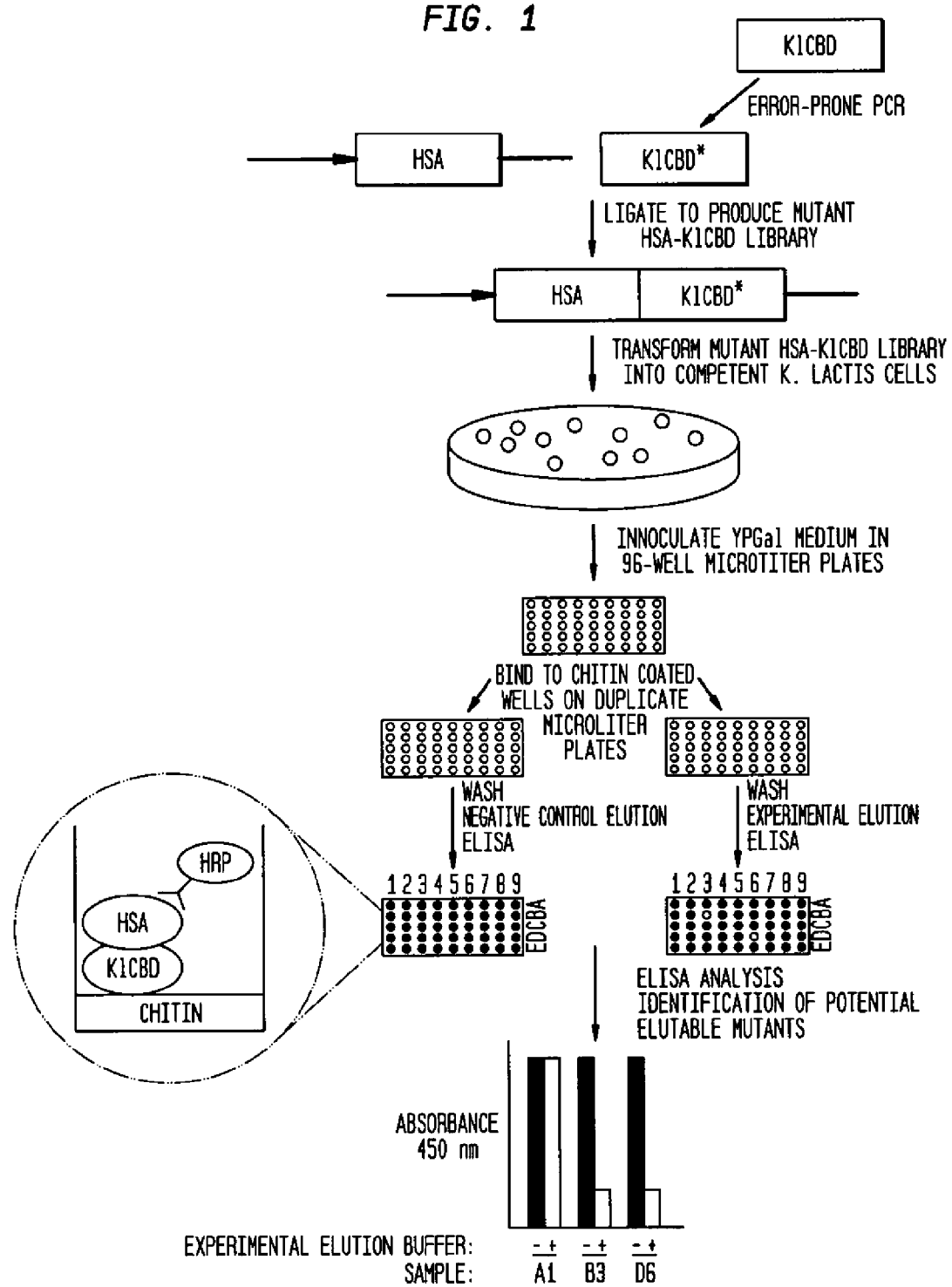
FIG. 1 shows a schematic of a method for obtaining mutant ChBD capable of elution under selected conditions.

Examples of mutants identified by the screening method of FIG. 1 to have a useful functionality include the *K. lactis* ChBD mutant (KlChBD$_{P1G2}$) that is elutable in a reducing buffer containing either DTT or β-mercaptoethanol. *K. lactis* ChBD$_{P1G2}$ binds to chitin in spent media. Washing of the bound chitin may be achieved using a Tris buffer and optionally including as much as 1M NaCl. For eluting the ChBD from the chitin, a buffer including a reducing agent at pH of 8-9 may be used. Binding of KlChBD$_{P1G2}$ fusion protein to insoluble chitin occurred directly in spent culture medium. Following binding to chitin, cells or spent culture media were washed away along with non-specific proteins in a neutral buffer or water that lacked substantially any reducing agent for KlChBD$_{P1G2}$ fusion protein.

The screening method was also used to identify a *Bacillus* ChBD mutant (BcChBD$_{M6}$) that acts as a transposable elutable affinity tag in buffer devoid of salt. This mutant BcChBD$_{m6}$ has two mutations and binds to chitin in spent medium without the need for adding any supplements. The spent medium contained small amounts of NaCl that facilitated binding of the BcChBD$_{M6}$ to chitin. Alternatively, BcChBD$_{M6}$ in a cell lysate can bind chitin in the presence of low levels of NaCl (<1M). The chitin-bound BcChBD$_{M6}$ can be washed to remove cells in which case, the medium used for washing may also include low levels of NaCl (for example, less than 1M NaCl). For eluting the ChBD from the chitin, a buffer containing little or no NaCl may be used.

Substantially pure protein can be eluted from the chitin substrate in the presence of reducing buffer in a pH range between 8 and 9 (KlChBD$_{P1G2}$ fusion protein) or 100 mM Tris-Cl pH range 8.0-9.0 (BcChBD$_{M6}$ fusion protein) (FIG. 3).

KlChBD$_{P1G2}$ or BcChBD$_{M6}$ can be used as an affinity tag on recombinant proteins that are either secreted or remain in the cytosol. These fusion proteins can be produced in any of the many prokaryotic or eukaryotic cells that are used in molecular biology applications. Examples of such cells include bacteria, yeast, mammalian and insect cells. KlChBD$_{P1G2}$ or BcChD$_{M6}$ are suitable affinity tags for secreted proteins while BcChBD$_{M6}$ is a suitable affinity tag for proteins made and retained in the cytoplasm of cells.

BcChBD$_{M6}$ fusion proteins expressed in the cytosol could be purified in a similar manner to secreted KlChBD$_{P1G2}$ fusion proteins. However, BcChBD$_{M6}$ fusion proteins bind to chitin in the presence of NaCl at concentrations that are equivalent to those found in normal spent medium. KlChBD$_{pig2}$ fusion proteins bind to chitin without additional additives. Elution of the KlChBD$_{pig2}$ fusion proteins from chitin was achieved by adding a reducing agent to eluant whereas the eluant used to elute BcChBD$_{M6}$ fusion proteins was an aqueous eluant lacking NaCl.

The binding of ChBD fusion proteins to chitin is a cost effective alternative to immunoprecipitation using protein A or G conjugated beads. For example, KlChBD$_{P1G2}$ or BcChBD$_{M6}$ precipitation and elution can be used to confirm the interaction of two known proteins or to isolate unknown proteins in a screen using bait KlChBD$_{P1G2}$ or BcChBD$_{M6}$ fusion proteins bound to chitin. In a further embodiment, KlChBD$_{P1G2}$ or BcChBD$_{M6}$ fusion proteins can be fixed to a solid support in a high throughput format such as 96-well chitin-coated microtiter plates. In this way protein interactions and complex formation between KlChBD$_{P1G2}$ or BcChBD$_{M6}$ fusion proteins and known or unknown proteins can be screened in a high throughput manner. Protein complexes can then be eluted for further analysis.

In summary, an advantage of a ChBD-chitin system of purification is that chitin is very abundant in the environment and provides a convenient and inexpensive matrix suitable for isolating proteins from cell lysates or large volumes of spent culture medium from fermentation. The ability to dissociate ChBD proteins from chitin has advantages in a number of molecular biology applications in addition to purification of desired protein. These include analysis of protein-protein interactions such as those commonly carried out by immunoprecipitation.

All references cited herein, as well as U.S. provisional application No. 60/718,657 filed Sep. 20, 2005, are hereby incorporated by reference.

EXAMPLES

Example 1

A Screen for ChBD Mutants that Conditionally Dissociate from Chitin

A library of randomly mutagenized DNA fragments encoding KlChBD or BcChBD were cloned into a *K. lactis* expression vector (pKLAC1) containing DNA encoding human serum albumin (pKLAC1-HSA) to create inframe fusions between the C-terminus and N-terminus of HSA and KlChBD or BcChBD mutants, respectively. An HSA PCR fragment was amplified with the forward primer CCGCTCGAGAAAAGAGATGCACACAAGAGTGAGGTTGCT (SEQ ID NO:5) and reverse primer CGCGGATCCTAAGCCTAAGGCAGCTTGACTTGC (SEQ ID NO:6) containing XhoI and BamHI restriction sites at their 5 prime ends, respectively.

The forward primer additionally contains two codons encoding lysine and arginine immediately 3' of the XhoI restriction site. These codons constitute the *K. lactis* Kex1 proteolytic cleavage site. This site provides an in-frame fusion of HSA with the *K. lactis* alpha-mating factor pre-pro leader sequence present in pKLAC1 that directs protein secretion and that is removed in a Kex1-dependent manner in the Golgi. A stop codon following the HSA coding region is not employed to allow for the subsequent in-frame fusion with mutant KlChBD or BcChBD DNA.

Random mutations are introduced into DNA encoding KlChBD or BcChBD by error-prone PCR in the following reaction mixture:

10 µl of 10× Thermopol II buffer (New England Biolabs, Inc., Ipswich, Mass.);

10 µl of 10× error-prone dNTP mix (2 mM dCTP, dTTP, 0.2 mM dGTP, dATP);

0.5 µg each of KlChBD forward primer CGGGGTACCGACTCCTGGGCTGTTACAAGA (SEQ ID NO:7) and KlChChBD reverse primer ATAAGAATGCGGCCGCGAAGACGACGTCGGGTTTCAAATA (SEQ ID NO:8) (containing 5' KpnI and NotI restriction sites, respectively) or BcChBD forward primer CGGGGTACCACGACAAATCCTGGTGTATCC (SEQ ID NO:9) and BcChBD reverse primer ATAAGAATGCGGCCGCTCATTGAAGCTGCCACAAGGCAGG (SEQ ID NO:10) (containing 5' KpnI and NotI restriction sites, respectively);

3 µl 100 mM MgCl$_2$;

5 µl 10 mM MnCl$_2$;

100 ng KlChBD or BcChBD template DNA; and

H$_2$O to a final volume of 99 µl.

This mixture was added to a 0.5 ml PCR tube and heated at 95° C. for 2 minutes followed by addition of 1 µl of Taq DNA polymerase (New England Biolabs, Inc., Ipswich, Mass.). To avoid overrepresentation of a single mutation generated in the early rounds of amplification the reaction mixture was divided into four 25 µl aliquots. Amplification progressed at 94° C. for 30 seconds, 50° C. for 30 seconds and 72° C. for 1 minute for 30 cycles and ended with a final 10-minute incubation at 72° C.

Amplified mutant KlChBD or BcChBD was cloned into the KpnI/NotI restriction sites of plasmid pKLAC1-HSA to form an in-frame fusion between the C- and N-terminus of the HSA and KlChBD or BcChBD proteins, respectively. A library consisting of approximately 9000 independent clones of mutant KlChBD fusions and 4400 independent clones of mutant BcChBD fusions were generated and amplified once. Sequence analysis of 20 randomly picked HSA-KlChBD mutant clones revealed the library averages 3.7 base pair and 2.5 amino acid changes per KlChBD clone. Sequence analysis of 10 randomly picked HSA-BcChBD mutant clones revealed the library averages 7 base pair and 3.5 amino acid changes per BcChBD clone.

Chemically competent *K. lactis* cells (New England Biolabs, Inc., Ipswich, Mass.) were transformed with 1 µg SacII linearized library DNA according to the manufacturers instructions and clones containing integrated vector DNA were selected on agar plates containing 1.17% yeast carbon base (New England Biolabs, Inc., Ipswich, Mass.), 5 mM acetamide (New England Biolabs, Inc., Ipswich, Mass.) and 30 mM sodium phosphate buffer pH 7 at 30° C. Individual *K. lactis* colonies were used to inoculate 600 µg of YPGal media in each well of a 96 deep-well round bottom plate (Nalge Nunc International, Rochester, N.Y.). YPGal media contained 1% yeast extract, 2% peptone and 2% galactose. Plates were covered with AirPore™ tape sheets (Qiagen, Inc., Valencia, Calif.) and were grown in a 30° C. shaker for 72 hours. During this time 96 well chitin-coated microtiter plates were prepared. Briefly, 300 mg crab shell chitosan (Sigma-Aldrich, St. Louis, Mo.) was dissolved overnight at room temperature in 50 ml 0.1 M sodium acetate buffer pH 3. Dissolved chitosan is diluted 1:10 in 0.1 M acetic acid pH 5 and 25 µg was added to every well of a 96-well round bottom microtiter plate (Falcon No. 353911, Fisher Scientific, Rockford, Ill.). Five microliters of acetic anhydride (Sigma-Aldrich, St. Louis, Mo.) was added to each well and the mixture was allowed to dry in a fume hood overnight at room temperature. Dried chitin resin in the microtiter plates was washed 3 times with phosphate-buffered saline (PBS) and the wells were blocked with 200 µg of a 3% (w/v) bovine serum albumin solution in PBS overnight at 4° C. Wells were subsequently washed 3 times with 20 mM Tris-Cl pH 7.5.

Deep-well plates containing *K. lactis* transformants were centrifuged in a Beckman GS-15 centrifuge for 2 minutes at 2500 rpm to pellet cells. For the KlChBD mutant-based screen 50 µl of culture supernatant was transferred to duplicate blocked and washed chitin plates and incubated for 1 hour at room temperature. Wells were then washed 3 times with 20 mM Tris-Cl pH 7.5. To one set of chitin plates 80 µl of 20 mM Tris-Cl pH 7.5 was added to each well (control plate) and to the duplicate plate 80 µl of elution buffer (1 M NaCl, 0.5 M DTT, 200 mM Glycine, 20 mM Tris-Cl pH 7.5) was added (experimental plate). Plates were incubated at room temperature for 10 minutes and eluant was removed and replaced with fresh buffer twice more for a total of three elutions. Wells were washed 3 times with 20 mM Tris-Cl pH 7.5 and then once with 0.1 M $NaPO_4$ buffer pH 7.0. Forty microliters of horseradish peroxidase conjugated anti-HSA antibody (USBiological, Swampscott, Mass.) was added to each well of duplicate plates and incubated for 1 hour at room temperature. Wells were washed 3 times with 0.1 M $NaPO_4$ buffer pH 7.0 followed by the addition of 40 µl 1-Step™ Ultra TMB-ELISA reagent (Fisher Scientific, Rockford, Ill.) to each well and incubatied at room temperature for 5 minutes. ELISA reactions were terminated by the addition of 100 µl of 2 M $H_2SO_4$. ELISA readings were recorded at 450 nm on a Versa$_{max}$ microplate reader (Molecular Devices Corp., Sunnyvale, Calif.). Wells containing mutants that dissociated from chitin during elution showed reduced signal compared to those treated with a control buffer.

For the BcChBD mutant-based screen 50 µl of culture supernatant was transferred to blocked and washed chitin plates and incubated for 1 h at room temperature. Wells were washed 3 times with wash buffer (20 mM Tris-Cl pH 7.5, 1 M NaCl). Forty microliters of elution buffer (20 mM Tris-Cl pH 7.5) was added to each well and plates were incubated for 10 minutes at room temperature. Eluant was transferred to a fresh 96-well microtiter plate and the elution was repeated with the second eluant pooled with the first (80 µl in total) in the fresh microtiter plate. Three microliters of pooled eluant was blotted on a 96-grid piece of nitrocellulose and allowed to completely dry. The nitrocellulose was blocked for 1 hour at room temperature in a solution of PBS-T containing 5% (w/v) non-fat milk and then rinsed in PBS-T. The blot was probed with a horseradish peroxidase conjugated anti-HSA antibody (USBiological, Swampscott, Mass.) diluted 1:10,000 in PBS-T containing 5% (w/v) non-fat milk for 1 hour at room temperature. The blot was washed for 10 minutes three times with PBS-T. Protein-antibody complexes were visualized using LumiGlo detection reagents (Cell Signaling Technology, Beverly, Mass.).

Example 2

Identification of KlChBD$_{P1G2}$—a ChBD Mutant that Dissociates from Chitin in the Presence of Reducing Agent Two hundred HSA-KlChBD mutants were screened and one mutant, KlChBD$_{P1G2}$, was found to conditionally dissociate from chitin. KlChBD$_{P1G2}$ contains a single base change that results in the amino acid change G524S and a base deletion resulting in a frameshift that causes premature termination and changes in the three C-terminal amino acids F542L, T543L and Y544I (see FIG. 2A). These mutations resulted in the elution characteristics of KlChBD$_{P1G2}$. The serine residue in G524S can be conservatively replaced with a threonine to maintain elution characteristics.

Early termination of KlChBD at L545 in conjunction with the G524S mutation (see FIG. 2A) resulted in a mutant that has 40% elution efficiency compared to KlChBD$_{P1G2}$, suggesting that the KlChBD C-terminal seven amino acids play an important role in stabilizing the chitin-KlChBD interaction. Furthermore, the C-terminal 10 amino acids of KlChBD contain three aromatic amino acids (F542, Y544 and F551) that were either mutated into other amino acids (F542L, Y544I) or abolished (F551) due to the frameshift mutation in KlChBD$_{P1G2}$. While not wishing to be limited by theory, it is here suggested that the interaction between chitin and ChBDs may occur through hydrogen bonding and hydrophobic interactions at the chitin-ChBD interface mediated by aromatic residues on the ChBD where removal or mutation of the three C-terminal aromatic residues of KlChBD (F542, Y544, F551) may weaken the interaction with chitin that, in a cumulative effect with mutations at $G^{524}$, allows elution in reducing buffer in the aforementioned pH range.

Given the nature of the mutations and the elution characteristics of KlChBD$_{P1G2}$, the evolution of desired elution characteristics can be achieved with repeated screens of random mutations using KlChBD$_{P1G2}$ as the starting template and/or targeted mutagenesis of amino acids identified as important for the interaction between chitin and KlChBD. In this way, a ChBD mutant capable of being eluted from chitin at an approximately neutral pH or other pH in the range of pH 5-10 and/or with altered reducing buffer concentrations, can be obtained.

Example 3

Identification of BcChBD$_{M6}$—a ChBD Mutant that Elutes from Chitin in the Absence of Salt at pH 8-9

Nine hundred and sixty HSA-BcChBD mutants were screened and one mutant, BcChBD$_{M6}$, was found to conditionally dissociate from chitin. BcChBD$_{M6}$ fusion proteins bound to chitin directly in spent yeast culture medium and remained bound upon washing with buffers containing 1 M NaCl. Dissociation from chitin occurred in buffers lacking salt that were in a pH range of between 8 and 9. The BcChBD$_{M6}$ mutant was found by sequencing to contain two point mutations resulting in P680H and V692I amino acid changes. The requirements for elution of BcChBD$_{M6}$ were established by examining the two mutations separately or together.

Example 4

Use of KlChBD$_{P1G2}$ and BcChBD$_{M6}$ in Purification of Proteins Secreted from Yeast KlChBD$_{P1G2}$ and BcChBD$_{M6}$ mutants were used to purify proteins as described below. A 1 ml column volume of chitin resin (New England Biolabs, Inc., Ipswich, Mass.) was washed with 10 column volumes of $H_2O$ and mixed with 10 ml of spent culture medium from yeast strains grown in YPGal and secreting HSA-KlChBD$_{P1G2}$, MBP-KlChBD$_{P1G2}$, HSA-BcChBD$_{M6}$ or MBP-BcChBD$_{M6}$. Chitin-culture medium samples were rotated for 1 hour at room temperature. Chitin resin was poured into a disposable Poly-Prep® Chromatography Column (Bio-Rad Laboratories, Hercules, Calif.) and washed with 10 ml of $H_2O$ for $KlChBD_{P1G2}$ fusion proteins or 10 ml of a 20 mM Tris-Cl pH 7.5, 1 M NaCl solution for $BcChBD_{M6}$ fusion proteins. One hundred microliters of chitin resin was removed for analysis by SDS-PAGE and Western analysis (Post-binding; PB sample). One column volume of elution buffer was added to the column and the eluant ($E_0$) was collected. For $KlChBD_{P1G2}$ fusion proteins elution buffers contained either 0.5 M DTT, 100 mM NaCl, 200 mM Tris-Cl pH 9 or 100 mM β-mercaptoethanol, 100 mM NaCl, 200 mM Tris-Cl pH 9. For $BcChBD_{M6}$ fusion proteins elution buffers consisted of 100 mM Tris-Cl pH 8.0 to 9.0. The column was then capped and another column volume of elution buffer was added to the resin and incubated for 10 minutes at room temperature. The cap was released and the eluant collected ($E_1$). This was repeated to collect the desired amount of fractions. The column was then washed with 10 ml of $H_2O$ for KlChBD fusion proteins or 10 ml of a solution containing 20 mM Tris-Cl pH 7.5, 1 M NaCl for $BcChBD_{M6}$ fusion proteins. A further 100 μl of chitin resin was removed for analysis by SDS-PAGE and Western analysis (Post-elution; PE sample). Elution characteristics for HSA-$KlChBD_{P1G2}$ and MBP-$KlChBD_{P1G2}$ fusion proteins were similar as shown in FIG. 3A and for HSA-$BcChBD_{M6}$ (FIG. 3B). This purification method or modifications of it could be used to affinity purify $KlChBD_{P1G2}$ or $BcChBD_{M6}$ tagged fusion proteins secreted from other species of yeast such as, but not limited to, *Pichia pastoris, Saccharomyces cerevisiae, Schizosaccharomyces pombe, Ifansenula polymorpha* and *Yarrowia lipolytica*.

Example 5

Use of $KlChBD_{P1G2}$ or $BcChBD_{M6}$ in Purification of Proteins Secreted from Organisms Other than Yeast $KlChBD_{P1G2}$ or BcChBD can be used as a chitin-based affinity tag for the purification of recombinant fusion proteins secreted from organisms other than yeast. These may include, but are not limited to, proteins secreted from mammalian cells or insect cells infected with a baculovirus expression vector. In either case, extracellular fusion protein is affinity purified from spent culture medium in a process similar to that used for the purification of $KlChBD_{P1G2}$- or $BcChBD_{M6}$-tagged proteins secreted from *K. lactis* or *Bacillus*.

Example 6

Use of $BcChBD_{M6}$ in Purification of Proteins Expressed in the Cytosol $BcChBD_{M6}$ is convenient for purification of recombinant fusion proteins produced in prokaryotic systems such as *E. coli* because wild-type BcChBD is currently commercially available as a component of the intein-mediated purification procedure IMPACT™ (New England Biolabs, Inc., Ipswich, Mass.). For $BcChBD_{M6}$ fusion protein purification lysate buffers contain an appropriate concentration of NaCl to allow binding to chitin.

What is claimed is:

1. A method of screening for a mutant carbohydrate-binding protein having altered binding affinity for a carbohydrate; comprising:
   (a) forming a library of cell clones expressing a carbohydrate-binding protein that has been mutated; and
   (b) identifying the altered binding affinity of the mutated carbohydrate binding protein for a carbohydrate-coated matrix, the binding affinity being different from the carbohydrate-binding protein without the mutation, wherein the mutant carbohydrate binding protein comprises a mutated domain selected from a mutated chitin binding domain and a mutated maltose-binding domain.

2. A method according to claim 1, wherein the mutant carbohydrate-binding domain is a chitin-binding domain and the carbohydrate is chitin.

3. A method according to claim 1, wherein the altered binding affinity is determined by an ELISA assay to determine bound fusion protein after applying the defined conditions for elution from the carbohydrate.

4. A method according to claim 1, wherein the altered binding affinity is determined by a Western blot assay to determine bound fusion protein after applying the defined conditions for elution from the carbohydrate.

5. A method according to claim 1, wherein the expressed protein is a fusion protein comprising the mutated carbohydrate protein and a reporter protein.

6. A method according to claim 1, wherein the library is a yeast cell library.

7. A method according to claim 5, wherein the yeast is *Kluyveromyces*.

8. A method according to claim 2, wherein the chitin is coated on a matrix selected from chitin-coated beads, chitin-coated columns and chitin-coated microtiter plates.

9. A method according to claim 1, wherein the defined conditions are non-denaturing conditions.

10. A method according to claim 9, wherein the non-denaturing conditions comprise a selected pH range or a reducing agent.

\* \* \* \* \*

SEQUENCE LISTING

<160> NUMBER OF SEQ ID NOS: 10

<210> SEQ ID NO 1
<211> LENGTH: 82
<212> TYPE: PRT
<213> ORGANISM: unknown
<220> FEATURE:
<223> OTHER INFORMATION: wild type chitin-binding domain from K. lactis
      (KlCTSI)

<400> SEQUENCE: 1

Asp Ser Trp Ala Val Thr Arg Ala Lys Glu Leu Asn Glu Gln Phe Val
1               5                   10                  15

Lys Gly Glu Leu Asn Gly Lys Asp Ser Cys Ser Asp Gly Glu Ile Ser
            20                  25                  30

Cys Thr Ala Asp Gly Lys Ile Ala Ile Cys Asn Tyr Gly Ala Trp Val
        35                  40                  45

Tyr Thr Glu Cys Ala Ala Gly Thr Thr Cys Phe Ala Tyr Asp Ser Gly
    50                  55                  60

Asp Ser Val Tyr Thr Ser Cys Asn Phe Thr Tyr Leu Lys Pro Asp Val
65                  70                  75                  80

Val Phe

<210> SEQ ID NO 2
<211> LENGTH: 75
<212> TYPE: PRT
<213> ORGANISM: unknown
<220> FEATURE:
<223> OTHER INFORMATION: mutated chitin-binding domain from K. lactis
      (KlCTSI)

<400> SEQUENCE: 2

```
Asp Ser Trp Ala Val Thr Arg Ala Lys Glu Leu Asn Glu Gln Phe Val
1               5                  10                  15

Lys Gly Glu Leu Asn Gly Lys Asp Ser Cys Ser Asp Gly Glu Ile Ser
                20                  25                  30

Cys Thr Ala Asp Gly Lys Ile Ala Ile Cys Asn Tyr Gly Ala Trp Val
            35                  40                  45

Tyr Thr Glu Cys Ala Ala Ser Thr Thr Cys Phe Ala Tyr Asp Ser Gly
    50                  55                  60

Asp Ser Val Tyr Thr Ser Cys Asn Leu Leu Ile
65                  70                  75

<210> SEQ ID NO 3
<211> LENGTH: 52
<212> TYPE: PRT
<213> ORGANISM: unknown
<220> FEATURE:
<223> OTHER INFORMATION: wild type chitin-binding domain from Bacillus
      circulans ChiAI

<400> SEQUENCE: 3

Thr Thr Asn Pro Gly Val Ser Ala Trp Gln Val Asn Thr Ala Tyr Thr
1               5                  10                  15

Ala Gly Gln Leu Val Thr Tyr Asn Gly Lys Thr Tyr Lys Cys Leu Gln
                20                  25                  30

Pro His Thr Ser Leu Ala Gly Trp Glu Pro Ser Asn Val Pro Ala Leu
            35                  40                  45

Trp Gln Leu Gln
    50

<210> SEQ ID NO 4
<211> LENGTH: 52
<212> TYPE: PRT
<213> ORGANISM: unknown
<220> FEATURE:
<223> OTHER INFORMATION: mutated chitin-binding domain from Bacillus
      circulans ChiAI

<400> SEQUENCE: 4

Thr Thr Asn Pro Gly Val Ser Ala Trp Gln Val Asn Thr Ala Tyr Thr
1               5                  10                  15

Ala Gly Gln Leu Val Thr Tyr Asn Gly Lys Thr Tyr Lys Cys Leu Gln
                20                  25                  30

His His Thr Ser Leu Ala Gly Trp Glu Pro Ser Asn Ile Pro Ala Leu
            35                  40                  45

Trp Gln Leu Gln
    50

<210> SEQ ID NO 5
<211> LENGTH: 39
<212> TYPE: DNA
<213> ORGANISM: unknown
<220> FEATURE:
<223> OTHER INFORMATION: primer

<400> SEQUENCE: 5
ccgctcgaga aaagagatgc acacaagagt gaggttgct                        39

<210> SEQ ID NO 6
<211> LENGTH: 33
<212> TYPE: DNA
<213> ORGANISM: unknown
<220> FEATURE:
```

-continued

```
<223> OTHER INFORMATION: primer

<400> SEQUENCE: 6
cgcggatcct aagcctaagg cagcttgact tgc                               33

<210> SEQ ID NO 7
<211> LENGTH: 30
<212> TYPE: DNA
<213> ORGANISM: unknown
<220> FEATURE:
<223> OTHER INFORMATION: primer

<400> SEQUENCE: 7
cggggtaccg actcctgggc tgttacaaga                                  30

<210> SEQ ID NO 8
<211> LENGTH: 40
<212> TYPE: DNA
<213> ORGANISM: unknown
<220> FEATURE:
<223> OTHER INFORMATION: primer

<400> SEQUENCE: 8
ataagaatgc ggccgcgaag acgacgtcgg gtttcaaata                       40

<210> SEQ ID NO 9
<211> LENGTH: 30
<212> TYPE: DNA
<213> ORGANISM: unknown
<220> FEATURE:
<223> OTHER INFORMATION: primer

<400> SEQUENCE: 9
cggggtacca cgacaaatcc tggtgtatcc                                  30

<210> SEQ ID NO 10
<211> LENGTH: 40
<212> TYPE: DNA
<213> ORGANISM: unknown
<220> FEATURE:
<223> OTHER INFORMATION: primer

<400> SEQUENCE: 10
ataagaatgc ggccgctcat tgaagctgcc acaaggcagg                       40
```